United States Patent
Fleischer

(10) Patent No.: US 7,046,348 B2
(45) Date of Patent: May 16, 2006

(54) DEVICE FOR MEASURING COLOR, LUSTER AND UNDULATIONS ON LACQUERED FREEFORM SURFACES

(75) Inventor: Johannes Fleischer, Berlin (DE)

(73) Assignee: X-Rite GmbH, Berlin (DE)

( * ) Notice: Subject to any disclaimer, the term of this patent is extended or adjusted under 35 U.S.C. 154(b) by 250 days.

(21) Appl. No.: 10/257,286

(22) PCT Filed: Jul. 28, 2001

(86) PCT No.: PCT/EP01/08778

§ 371 (c)(1),
(2), (4) Date: Jul. 2, 2003

(87) PCT Pub. No.: WO02/27298

PCT Pub. Date: Apr. 4, 2002

(65) Prior Publication Data

US 2003/0234920 A1    Dec. 25, 2003

(30) Foreign Application Priority Data

Sep. 29, 2000  (DE) ............................... 100 48 723
Mar. 21, 2001  (DE) ............................... 101 13 846

(51) Int. Cl.
  *G01N 21/25* (2006.01)
(52) U.S. Cl. ..................... 356/73; 356/402; 356/603
(58) Field of Classification Search ............ 356/73, 356/402, 601, 603
See application file for complete search history.

(56) References Cited

U.S. PATENT DOCUMENTS 4,989,984 A * 2/1991 Salinger .................. 356/445
6,507,036 B1 * 1/2003 Godin .................... 356/73

FOREIGN PATENT DOCUMENTS

DE    19758260 A  *  7/1999
EP    0726456 A   *  8/1996

OTHER PUBLICATIONS

Patent Abstracts of Japan, vol. 011, No. 178 (p. 584), Jun. 9, 1987—JP62008042 (Nissan Motor Co. Ltd) Jan. 16, 1987.*

* cited by examiner

*Primary Examiner*—F. L. Evans
(74) *Attorney, Agent, or Firm*—Antonelli, Terry, Stout and Kraus, LLP.

(57) ABSTRACT

The invention relates to a device for measuring color, luster and undulations on lacquered freeform surfaces at a predetermined target distance and symmetrically in relation to the measuring point normal lines at a measuring point. Said device is characterized by the provision of a measuring head that can be displaced in three dimensions by at least one motor and that comprises a measuring-head axis, a light emitter and a video camera. The light emitter is provided with a planar light pattern that is to be emitted along its illumination axis. An evaluation unit is provided for the light pattern (reproduction pattern) of the light emitter that is reproduced in the video camera, said evaluation unit emitting a control signal which is dependent on and formed from the distortion produced or the migration of the reproduction pattern. The measuring head is provided with a motor control, to whose input the control signal of the evaluation unit is applied and the measuring head is displaced in order to reduce the distortion or the migration of the reproduction pattern in the video camera to below a predetermined value, in such a way that both the measuring head axis coincides with the measuring point normal lines and the vertex of the angle formed by the illumination axis of the light emitter and the optical axis of the video camera coincides with the measuring point.

13 Claims, 2 Drawing Sheets

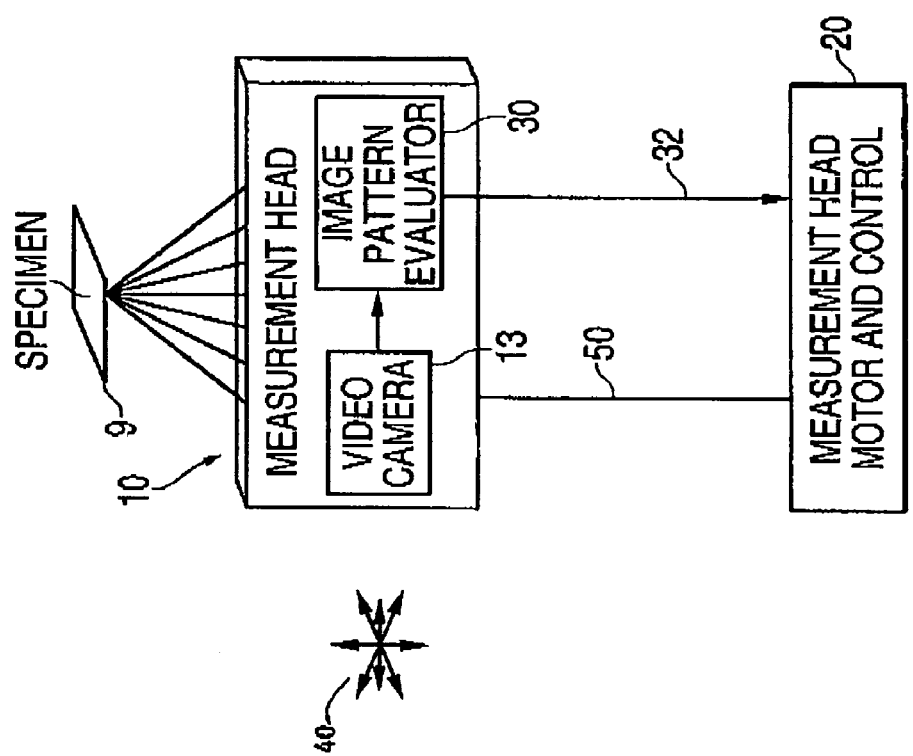

DEVICE FOR MEASURING COLOR, LUSTER AND UNDULATIONS ON LACQUERED FREEFORM SURFACES

BACKGROUND OF THE INVENTION

1. Field of the Invention

The invention relates to a device for measuring color, and optionally luster and undulations on enamelled freeform surfaces at a definable setpoint distance and symmetrically to the surface normals at the measurement point, the measurement point normals.

2. Description of the Prior Art

Devices for measuring color, luster and undulation on enamelled freeform surfaces are handheld and used for random sample measurements of for example automobile bodies coming from enamelling. This measurement is extremely difficult in frequently occurring metallic enamelling since the surfaces to be measured on the automobile are almost never plane. For greater curvatures of the surface precise color measurement with these known devices is not possible, quite aside from the fact that these measurements are very intensive in terms of time and personnel. In any case, the known hand measurement devices must be used with physical contact with the measurement surface. Since distance changes of 0.1 mm and angle changes of 0.1 degree, which can easily occur when the measurement devices are tilted in a measurement on curved surfaces, greatly influence the measurement result making these manual measurements extremely inaccurate. But the greatest defect is, as was initially mentioned, that measurement is not possible without contact, because otherwise the measurement inaccuracies become too great.

SUMMARY OF THE INVENTION

Therefore the object of the invention is to develop a generic device such that noncontact measurement is possible.

In a generic device in accordance with the invention, this object is achieved. The device comprises a measurement head which can be moved in three dimensions, with one measurement head axis, an opto-transmitter, a video camera with an optical axis, the opto-transmitter having a two-dimensional light pattern which is transmitted along an emission axis, the measurement head axis, the emission axis and the optical axis lying in one plane and the measurement head axis forming the bisector of an angle which is formed by the emission axis and the optical axis, an evaluation means for the light pattern imaged on the video camera (imaging pattern) of the opto-transmitter, which delivers a control signal which is formed by and dependent on distortion or migration of the image pattern which is caused as a result of no setpoint distance and/or no symmetry to the measurement point normals, and a motor control for the measurement head with an input of the control signal which causes motion of the measurement head to reduce distortion or migration of the imaging pattern in the video camera to under a definable amount.

With the device of the invention it is possible to measure enamelled freeform surfaces with respect to their color and optionally luster and/or undulation. To do this, the measurement head first determines at the measurement point the surface normal as the measurement point normal such that the measurement head axis coincides with it. Moreover, due to distortion or migration of the imaging pattern, an integrated circuit of the video camera can determine the correct distance of the measurement head from the measurement point by specifically the vertex of the angle between the emission axis and the optical axis of the video camera forming exactly the measurement point. In one embodiment however, on the measurement head there can be an additional distance measuring device, for example an ultrasonic measurement head function to provide a rough setting, when the device is roughly placed before the surface normal at the measurement point. When the measurement head is aligned by the control signals of the evaluation device for motor control, the actual measurement can begin.

To do this, in the measurement head there is another light source with an optical exit axis which preferably includes within the measurement head axis an angle of 45 degrees. The light of this measurement head axis from at least one other (preferably four other monochromators) is arranged at definable angles with their optical entry axis to the measurement head axis such that all the optical entry axes of the monochromators, the axis of the measurement head and the optical exit axis of the other light source are located in one plane, which is not necessarily the same plane of the emission axis of the opto-transmitter and the optical axis of the video camera. Then, parallel thereto, via the four monochromators, the color and/or the luster of the enamelled freeform surface at the measurement point can be ascertained.

BRIEF DESCRIPTON OF THE DRAWING

One embodiment of the invention is described below with reference to the drawings which shows a device in a schematic perspective and the housing partially removed.

FIG. 2 is a block diagram of the invention.

DESCRIPTION OF THE PREFERRED EMBODIMENT

Figure 1:
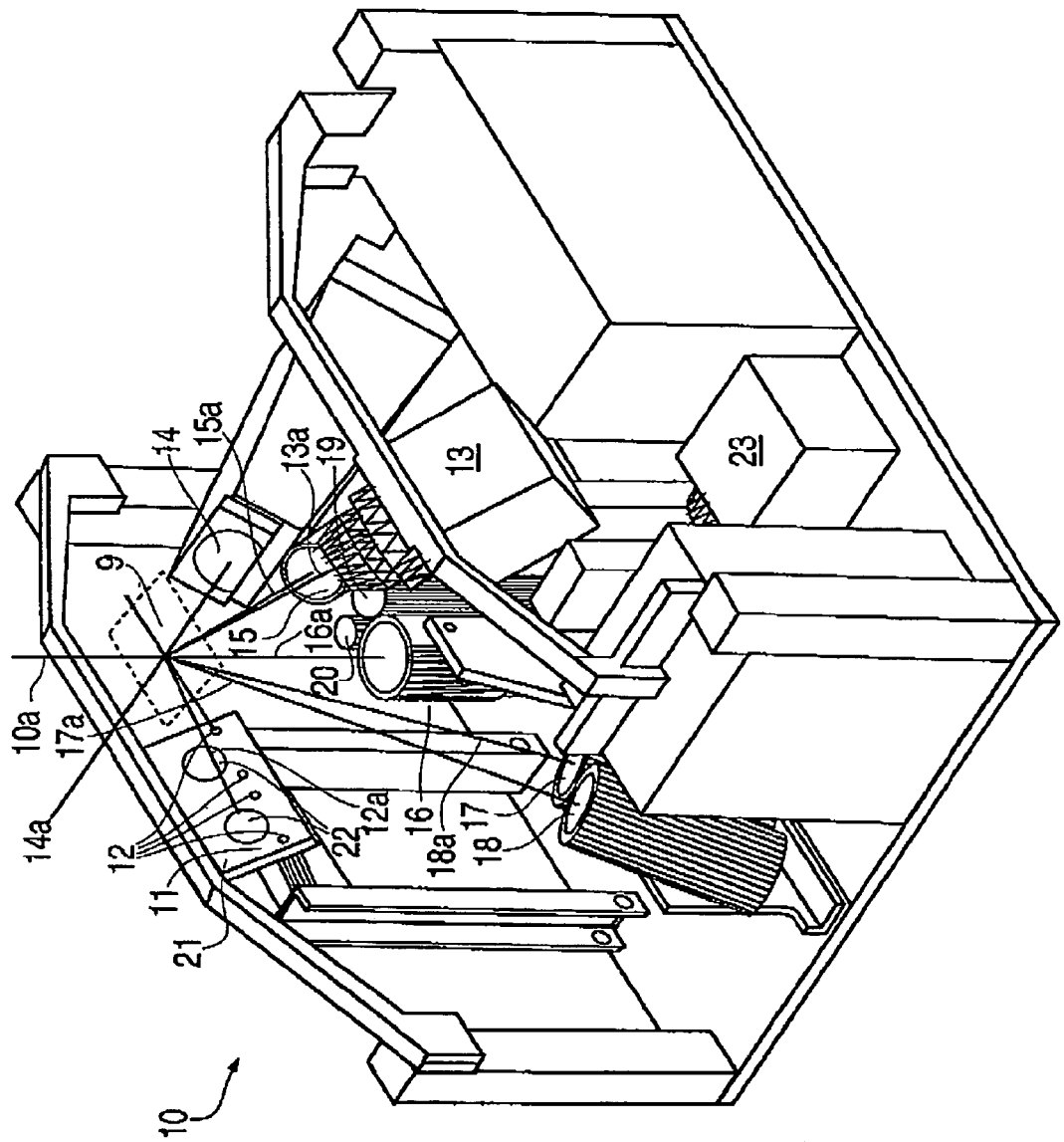
FIG. 1 is an illustration of an embodiment of the measurement head.

The device for measurement of the color on enamelled freeform surfaces at a definable setpoint distance and symmetrically to the measurement point normal has a measurement head which is labelled 10 overall and which is provided with a measurement head axis 10a. The measurement head 10, which can be moved overall in three dimensions by a measurement head motor and control 20 in combination with any suitable coupling mechanism illustrated symbolically by line 50, is provided with an opto-transmitter which is labelled 11 and a video camera 13 which receives its two-dimensional light pattern 12 to be sent, and which has an optical axis 13a aligned in the direction to the specimen labelled 9 overall. The light pattern 12 is provided with an emission axis which is labelled 12a and which is likewise aligned at the specimen 9.

Here the optical axis 13a, the emission axis 12a and the measurement head axis 10a lie in one plane, the measurement head axis 10a forming the bisector to the angle formed by the emission axis 12 and the optical axis 13a of the video camera 13.

Furthermore, there is an image pattern evaluator 30 (evaluation means) coupled to the output of video camera 13 which provides an evaluation of the two-dimensional image pattern of the opto-transmitter 12 imaged on the video camera. The evaluator 30 delivers a control signal 32 which is formed by and dependent on the distortion or migration of the image pattern caused as a result of the absence of a setpoint distance and/or symmetry to the measurement point normal. This control signal 32 is applied to the measurement head motor and control 20 for the measurement head 10, by which three-dimensional motion 40 is applied to the measurement head 10 by the coupling mechanism 50. Three dimensional motion 40 of the measurement head occurs in the sense of reducing of the distortion or the migration of the image pattern in the video camera 13 to under a definable amount such that both the measurement head axis 10a and also the vertex of the angle formed by the emission axis 12a of the opto-transmitter 12 and the optical axis 13a of the video camera 13 coincide with the measurement point, specifically the specimen 9. In the measurement head there is another light source 14 with an optical exit axis 14a which includes an angle of 45° with the device axis 10a.

Furthermore, in the measurement head 10 there are four monochromators 15, 16, 17, 18 which are aligned at definable specific angles with their optical entry axis 15a, 16a, 17a, and 18a. All these optical entry axes 15a, 16a, 17a and 18a are aligned to the measurement point 9 and lie in another plane in which the optical exit axis 17a of the other light source 14 also lies. Here the surface normals of the plane and the surface normals of the latter other plane are arranged at a right angle to one another. Moreover there is an infrared thermometer 19 aligned to the measurement point and optionally an ultrasonic sensor 20 for rough distance setting in the measurement head 10.

Furthermore, the light points 12 of the opto-transmitter 11 are formed on plate 21 which also has two openings 22. The light points 12 are spaced apart from each other on plate 21.

Furthermore, in the measurement head 10 there is another camera 23, which via a mirror (not visible in the drawings) located in the area of the measurement head axis 10a, images an image of the measurement point or the specimen 9 with two bright stripes on a black background. A Fourier breakdown of the image yields the degree of undulation or luster.

All the measurement signals and measurement values can be plotted and stored and optionally delivered on-line via an interface to a process computer.

The invention claimed is:

1. A device for measuring color, luster and undulation on enamelled freeform surfaces at a definable setpoint distance and symmetrically to measurement point normals at a measurement point, comprising a measurement head which is movable in three dimensions by at least one motor, a measurement head axis, a video camera, an opto-transmitter with a light pattern which is sent along an emission axis, the video camera having an optical axis, the measurement head axis, the emission axis and the optical axis lying in one plane, and the measurement head axis forming a bisector of an angle which is formed by the emission axis and the optical axis, an evaluation means for the light pattern imaged in the video camera by the opto-transmitter, evaluation means providing a control signal which is dependent on distortion or migration of the light pattern that is caused as a result of an absence of a setpoint distance and/or symmetry to measurement point normals, a motor control for the measurement head including an input of the control signal which causes motion of the measurement head to reduce distortion or migration of the light pattern imaged in the video camera to under a desired amount, such that both the measurement head axis with the measurement point normals and a vertex of the angle formed by an emission axis of the opto-transmitter and the optical axis of the video camera coincides with the measurement point.

2. A device as claimed in claim 1, comprising:
another light source in the measurement head.

3. A device as claimed in claim 2, comprising:
an optical exit axis of the another light source includes within the measurement head axis an angle of 45 degrees.

4. A device as claimed in claim 2, comprising:
monochromators arranged in the measurement head aligned at angles with optical entry axes thereof relative to the measurement head axis.

5. A device as claimed in claim 4, wherein:
the optical exit axis of the another light source and the optical entry axes of the monochromators are aligned to the measurement point.

6. A device as claimed in claim 5, wherein:
the optical exit axis of the another light source and the optical entry axes of the monochromators and the measurement head axis lie in another plane.

7. A device as claimed in claim 6, wherein:
surface normals of the one plane and surface normals of the another plane form a right angle to one another.

8. A device as claimed in claim 1, comprising:
an infrared thermometer in the measurement head aligned for measuring temperature at the measurement point.

9. A device as claimed in claim 1, wherein:
the light pattern of the opto-transmitter is transmitted from a plate.

10. A device as claimed in claim 9, wherein:
the light pattern has light points spaced apart from one another on the plate.

11. A device as claimed in claim 1, wherein:
the measurement head has an ultrasonic measurement head providing a rough setting of the measurement head placed before a surface normal at the measurement point determined as one of the measurement point normals.

12. A device as claimed in claim 1, wherein:
the evaluation means computes from existing distortion or migration of the image pattern a first approximation of a correction provided to the motor control for causing adjustment of distortion or migration, after which the evaluation means iteratively computes additional approximations from resulting new image patterns until the image pattern is enlarged or diminished by an imaging scale of the video camera corresponding to a shape of the light pattern of the opto-transmitter.

13. A device as claimed in claim 1, wherein:
another camera located relative to measurement head axis receives via a mirror an image of a measurement point with two bright stripes on a black background and Fourier analysis yields a degree of undulation or luster.

* * * * *